US008568303B2

(12) United States Patent  (10) Patent No.: US 8,568,303 B2
Yamane  (45) Date of Patent: *Oct. 29, 2013

(54) SUCTION CONDUIT DEVICE OF ENDOSCOPE THAT PREVENTS CLOGGING

(75) Inventor: Kenji Yamane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 223 days.

This patent is subject to a terminal disclaimer.

(21) Appl. No.: 12/981,258

(22) Filed: Dec. 29, 2010

(65) Prior Publication Data

US 2011/0208003 A1 Aug. 25, 2011

(30) Foreign Application Priority Data

Feb. 24, 2010 (JP) ................. 2010-038225

(51) Int. Cl.
A61B 1/12 (2006.01)
(52) U.S. Cl.
USPC ............................ 600/159; 600/156; 600/158
(58) Field of Classification Search
USPC .................................................. 600/156–159
See application file for complete search history.

(56) References Cited

U.S. PATENT DOCUMENTS

| 1,527,872 | A | * | 2/1925 | Herrick | 604/249 |
| 2,638,108 | A | * | 5/1953 | Williams et al. | 137/102 |
| 4,412,531 | A | * | 11/1983 | Chikashige | 600/104 |
| 4,519,385 | A | * | 5/1985 | Atkinson et al. | 601/161 |
| 4,852,551 | A | * | 8/1989 | Opie et al. | 600/121 |
| 4,860,731 | A | * | 8/1989 | Matsuura | 600/157 |
| 5,226,885 | A | * | 7/1993 | Takahashi | 604/118 |
| 5,257,773 | A | * | 11/1993 | Yoshimoto et al. | 251/339 |
| 5,322,263 | A | * | 6/1994 | Yoshimoto et al. | 251/251 |
| 5,692,729 | A | * | 12/1997 | Harhen | 251/4 |
| 5,695,450 | A | * | 12/1997 | Yabe et al. | 600/123 |
| 5,840,015 | A | * | 11/1998 | Ogino | 600/159 |
| 5,871,441 | A | * | 2/1999 | Ishiguro et al. | 600/133 |
| 6,569,087 | B2 | * | 5/2003 | Naito et al. | 600/156 |
| 6,623,445 | B1 | * | 9/2003 | Nelson et al. | 604/35 |
| 2006/0041190 | A1 | * | 2/2006 | Sato | 600/159 |
| 2008/0027283 | A1 | * | 1/2008 | Matsui et al. | 600/127 |
| 2010/0049001 | A1 | * | 2/2010 | Yamane | 600/159 |

FOREIGN PATENT DOCUMENTS

JP  2004-223121 A  8/2004
JP  2007-185276 A  7/2007

* cited by examiner

Primary Examiner — Matthew J Kasztejna
(74) Attorney, Agent, or Firm — Birch, Stewart, Kolasc & Birch, LLP

(57) ABSTRACT

In a suction valve in which a suction conduit is connected from a treatment instrument insertion channel through a branch portion so as to open/close this suction conduit, there is no passage between a side face of a valve-portion passage in the valve and a side face of a piston shaft, but only the valve-portion passage and an inner-shaft passage of the piston shaft are used, and their diameters $d_3$ are made larger than a diameter $d_2$ of the suction conduit. Also, the diameter $d_2$ of the suction conduit is made larger than an inner diameter $d_1$ of the treatment instrument insertion channel. As a result, a suction load when a solid substance, a substance with high viscosity or the like is suctioned is reduced, and clogging by the suctioned substances in a passage in the suction valve is prevented.

4 Claims, 5 Drawing Sheets

SUCTION CONDUIT DEVICE OF ENDOSCOPE THAT PREVENTS CLOGGING

BACKGROUND OF THE INVENTION

The disclosure of Japanese Patent Applications No. 2010-38225 on Feb. 24, 2010, including its specification, claims and drawings, is incorporated herein by reference in its entirety.

1. Field of the Invention

The present invention relates to a suction conduit (tube) device or particularly to a suction tube communicating with a treatment instrument insertion channel and configurations of a suction tube and a suction valve of an endoscope in which the suction valve that opens/closes the suction tube is arranged.

2. Description of the Related Art

In an endoscope, a suction function (a suction conduit device) for suctioning a saline solution, blood, body tissues, body wastes and the like in the body using a treatment instrument insertion channel, a suction tube, and a suction valve or the like is disposed.

FIG. 5 shows an example (similar to Japanese Patent Laid-Open No. 2007-185276 (Document 1)) of a prior-art suction valve (suction control portion) constituting the suction conduit device, and in this suction valve, a piston shaft 2 is integrally fixed to a suction button 1 made of an elastic body, and this piston shaft 2 is arranged so as to move vertically through an internal passage (valve-portion passage) of a main body 3. On the lower side of this main body 3, a suction tube 4 is connected, and a suction pump is connected to a connection tube 5 formed so as to extend from the main body 3. Also, on a side wall of the suction button 1, an opening 1a for suctioning air is formed.

According to such suction valve, as shown in FIG. 5, by pressing the suction button 1, the piston shaft 2 is moved downward, and a valve portion 6 and an opening 2a of the piston shaft 2 are opened, whereby a suction operation by suctioning by the suction pump is performed, and the saline solution and the like present in the body is suctioned and discharged. Also, by releasing the pressing on the suction button 1, the valve portion 6 is closed, and the air is suctioned through the opening 1a of the suction button 1, and suctioning through the suction tube 4 is not performed.

However, with the prior-art suction conduit device of an endoscope, when solid substances or substances with high viscosity (such as coagulated blood, tissue pieces and the like) are to be suctioned from inside the body, there are problems that a large load is applied and a passage inside the suction valve might be clogged by the suctioned substances.

In the case of the suction valve in FIG. 5, since the passage of the valve portion 6, that is, a passage between the side face of the piston shaft 2 and the side face of the internal passage of the main body 1 is narrowed, this passage or its vicinity is clogged by the suctioned substances. And such clogging by the suctioned substances might incur a failure of the device or interruption of endoscopic observation or the like.

In the prior-art references, there is a conduit switching valve in which a passage is not formed between the side face of the piston and the side face of the internal passage of the main body (cylinder) as shown in Japanese Patent Laid-Open No. 2004-223121 (Document 2).

The present invention was made in view of the above problems and has an object to provide a suction conduit device of an endoscope that reduces a suction load when a solid substance, a substance with high viscosity or the like is suctioned and prevents clogging of the passage in the suction valve by the suctioned substances.

SUMMARY OF THE INVENTION

In order to achieve the above object, a suction conduit device of an endoscope according to the present invention has a treatment instrument insertion channel (also referred to as a forceps channel) arranged from a distal end portion to an operation portion of the endoscope and a suction conduit disposed from the treatment instrument insertion channel in the operation portion through a branch portion, and it is characterized in that, in the endoscope that performs suctioning through the treatment instrument insertion channel and the suction conduit, a suction valve that opens/closes the conduit by reciprocally moving a piston shaft through a valve-portion passage to which the suction conduit is connected and does not use a space between the valve-portion passage and a side face of the piston shaft as a passage but uses only the valve-portion passage and an inner-shaft passage formed in the piston shaft or only the valve-portion passage as a passage is disposed, and the diameter of the valve-portion passage of this suction valve and the diameter of the piston inner-shaft passage or the valve-portion passage of the suction valve is made larger than the diameter of the suction conduit.

In this invention, the diameter of the suction conduit may be made larger than the diameter of the treatment instrument insertion channel (forceps diameter) arranged on the distal end side from the branch portion.

Also, another invention is characterized in that, in an endoscope having the treatment instrument insertion channel arranged from the distal end portion to the operation portion of the endoscope and the suction conduit disposed from the treatment instrument insertion channel in the operation portion through the branch portion, in which suctioning is performed through the treatment instrument insertion channel and the suction conduit, the diameter of the suction conduit is made larger than the diameter of the treatment instrument insertion channel arranged on the distal end portion side from the branch portion.

In the above, the wording "large" refers to the largeness of 0.05 mm or larger in terms of diameter. Also, the diameters of the conduit and the passage refer to the minimum diameters of the conduit and the passage.

According to the configuration of the present invention, if there is no passage between the side face of the piston shaft and the side face of the valve-portion passage in the suction valve and only the valve-portion passage and the piston inner-shaft passage inside are disposed, the diameters of these passages become larger than the diameter of the suction conduit, and if only the valve-portion passage is disposed in the suction valve, the diameter of the valve-portion passage becomes larger than the diameter of the suction conduit. Moreover, by making the diameter of the suction conduit larger than the diameter of the treatment instrument insertion channel (forceps diameter) on the distal end portion side from the branch portion, when a solid substance, a substance with high viscosity or the like is to be suctioned, a suction load is reduced, and clogging by the suctioned substances is prevented.

Also, in the suction valve having a passage between the side face of the piston shaft and the valve-portion passage, by making the diameter of the suction conduit larger than the forceps diameter while making the passage wider than before, the suction load can be reduced, and clogging by the suctioned substances can be prevented.

According to the suction conduit device of an endoscope of the present invention, there are effects that a suction load is reduced when a solid substance, substances with high viscosity or the like is to be suctioned, the passage in the suction valve is prevented from being clogged by the suctioned substances, and a failure of the device, interruption of endoscopic observation and the like can be eliminated.

DESCRIPTION OF THE PREFERRED EMBODIMENTS

First Embodiment

Figure 1:
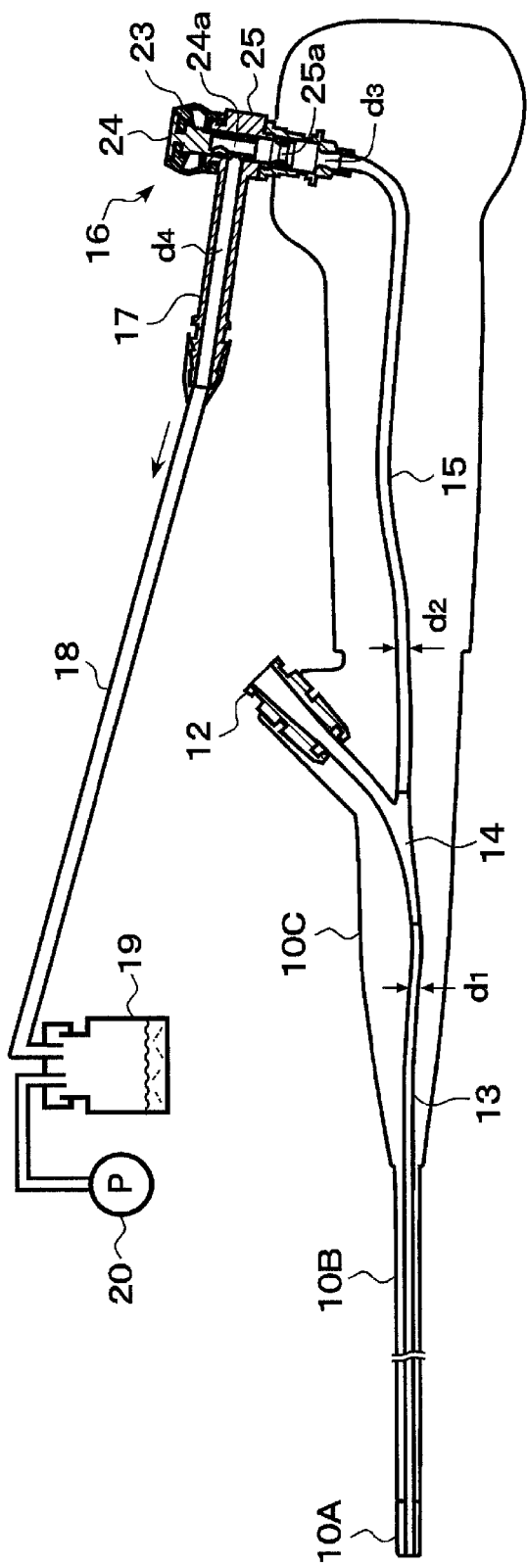
FIG. 1 is a view illustrating a configuration of a suction conduit device of an endoscope according to a first embodiment of the present invention.
Figure 2A:
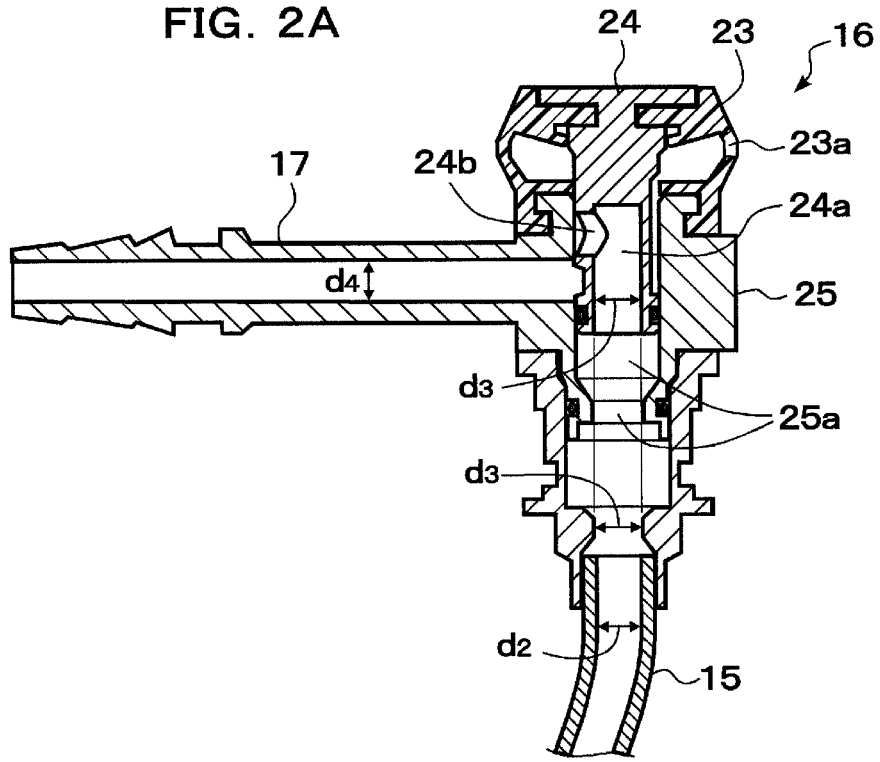
FIG. 2A is a sectional view of a closed state of a suction valve of the first embodiment.
Figure 2B:
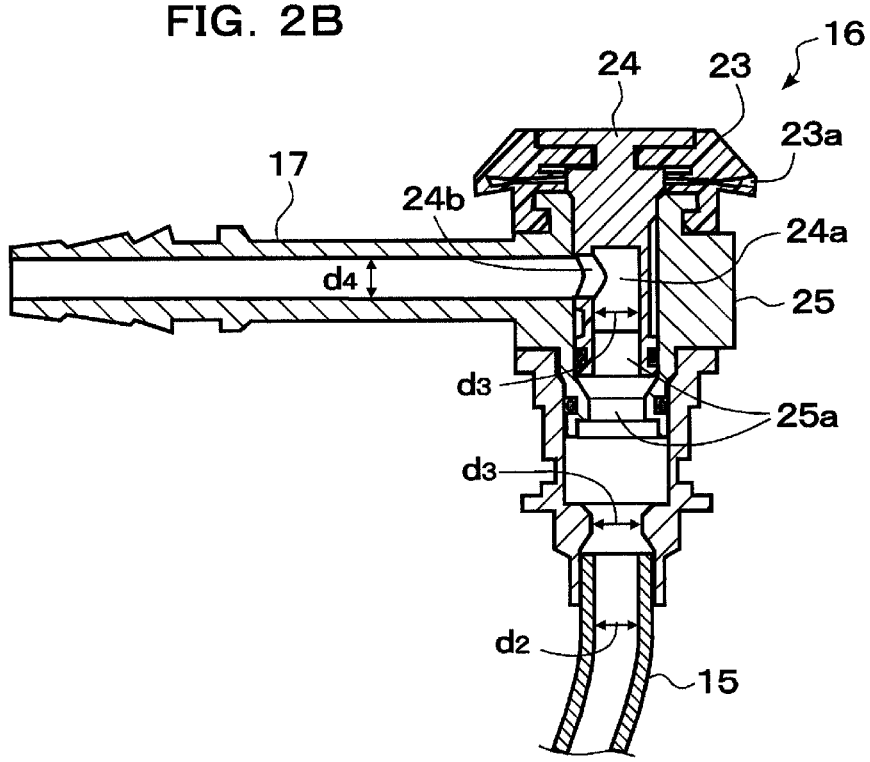
FIG. 2B is a sectional view of an open state of the suction valve of the first embodiment.

FIGS. 1, 2A and 2B show a suction conduit device of an endoscope according to a first embodiment of the present invention, and the suction conduit device of an endoscope of this first embodiment has, as shown in FIG. 1, a treatment instrument insertion channel 13 arranged from a distal end portion 10A to a forceps port (treatment instrument introduction port) 12 of an operation portion 10C through an insertion portion (flexible portion) 10B. In this treatment instrument insertion channel 13, a suction tube 15 is disposed through a branch portion (branch tube) 14, and to this suction tube 15, a suction valve 16 is connected. To a connection tube 17 of this suction valve 16, a preserving tank 19 for preserving suctioned substances is connected through an external suction tube (flexible pipe or the like) 18, and a suction pump 20 is connected to this preserving tank 19.

In such suction conduit device, a diameter of the suction tube 15 (an inner diameter or strictly speaking, the minimum diameter of a tube) $d_2$ is set larger than an inner diameter (hereinafter referred to as a forceps diameter) $d_1$ of the treatment instrument insertion channel 13 on the distal end side from the branch portion 14 (that is, it is made larger by 0.05 mm or more). As this forceps diameter $d_1$, for example, φ2.0 (diameter mm), φ2.2, φ2.8 and the like are used, but in this embodiment, the diameter $d_2$ of the suction tube 15 with respect to the treatment instrument insertion channel 13 having these forceps diameters $d_1$ is set at φ3.2. Also, though details will be described later, a diameter $d_3$ of the valve-portion passage in the suction valve 16 is set at φ3.5, which is larger than the diameter $d_2$ of the suction tube 15, and a diameter (inner diameter) $d_4$ of the connection tube 17 of the suction valve 16 and the external suction tube 18 is set at φ3.2.

FIGS. 2A and 2B show a detailed configuration of the suction valve 16, and this suction valve 16 is made of an elastic body and has a suction button 23 in which an opening 23a for suctioning air is formed, and a piston shaft 24 is integrally fixed to this suction button 23 and this piston shaft 24 is arranged so as to vertically move through a valve-portion passage 25a of a main body 25. In this piston shaft 24, an inner-shaft passage 24a is formed in the axial direction inside, and an opening 24b is formed in a side face, the suction tube 15 is connected to the lower side of the main body 25, and the connection tube 17 is formed so as to extend from the side face of the main body 25.

Therefore, this suction valve 16 is configured such that a passage is not formed between a side face (inner peripheral face) of the valve-portion passage 25a and a side face (outer peripheral face) of the piston shaft 24. And as mentioned above, the diameter $d_3$ of the valve-portion passage 25a inside the suction valve 16 and the inner-shaft passage 24a is set at φ3.5, which is larger than the diameter $d_2$ of the suction tube 15 and the diameter $d_4$ of the connection tube 17 at φ3.2.

The first embodiment is configured as above, and in this first embodiment, as shown in FIGS. 2A and 2B, when the suction button 23 is pressed, the piston shaft 24 is moved downward so as to arrange the opening 24b at the position of the connection tube 17 and to open it, whereby a suction operation by the suction pump 20 is performed, and solid substances, substances with high viscosity and the like present in the body are suctioned and discharged. On the other hand, if the pressing on the suction button 23 is released, the opening 24b is closed, whereby the air is suctioned through the opening 23a of the suction button 23, and suctioning through the treatment instrument insertion channel 13 is stopped.

In such a suctioning operation, the suctioned substances pass from the distal end portion 10A through the treatment instrument insertion channel 13 of the forceps diameter $d_1$ and the suction tube 15 of the inner diameter $d_2$ larger than this diameter $d_1$ and also passes through the valve-portion passage 25a and the inner-shaft passage 24a of the diameter $d_3$ larger than the diameter $d_2$ in the suction valve 16 and the external suction tube 18 (diameter $d_4$>$d_1$), and even the solid substances and suctioned substances with high viscosity are suctioned smoothly, and clogging by the suctioned substance in the suction tube 15 and the suction valve 16 does not occur any longer.

Second Embodiment

Figure 3:
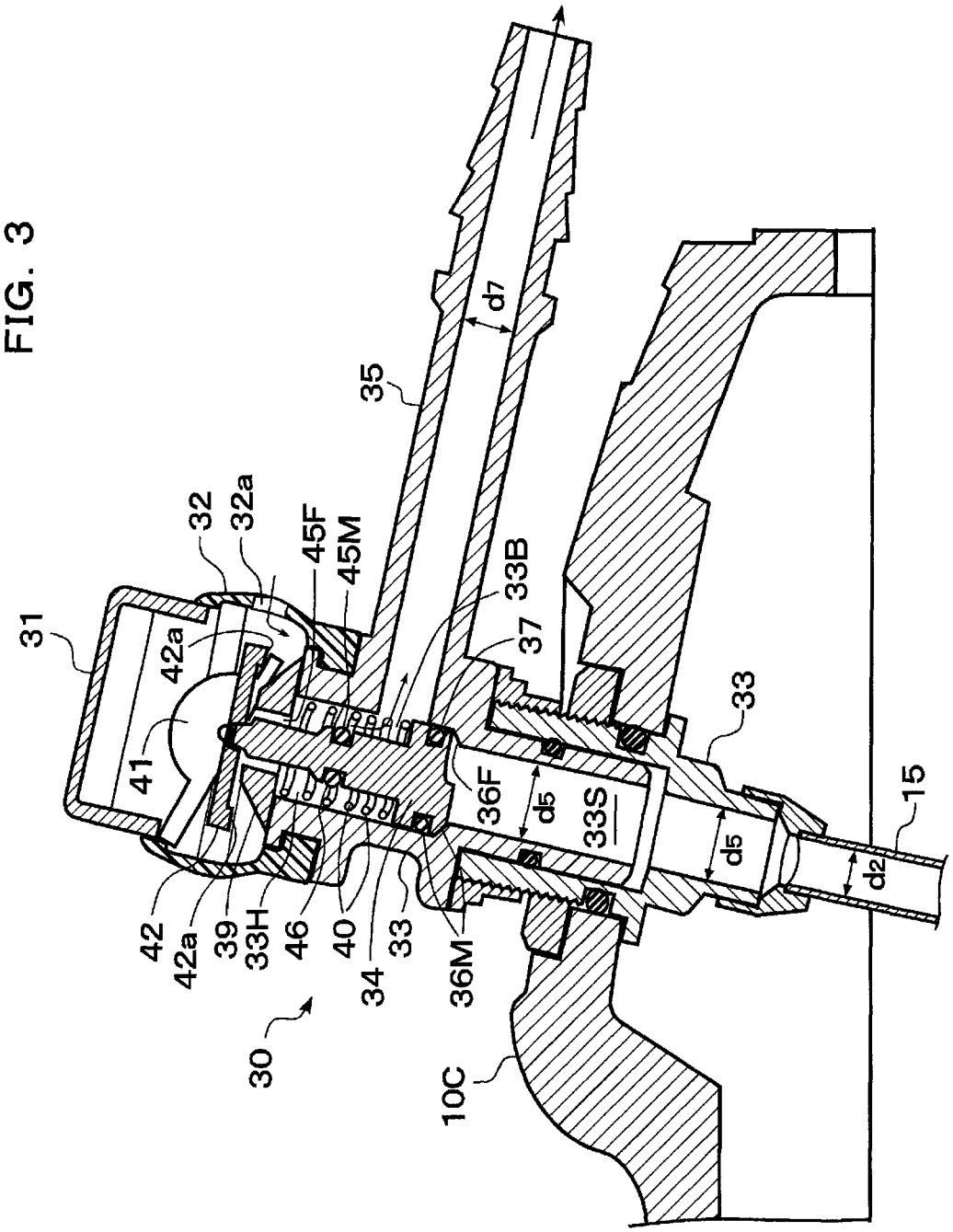
FIG. 3 is a sectional view illustrating a configuration of a closed state of a suction valve of a second embodiment.
Figure 4:
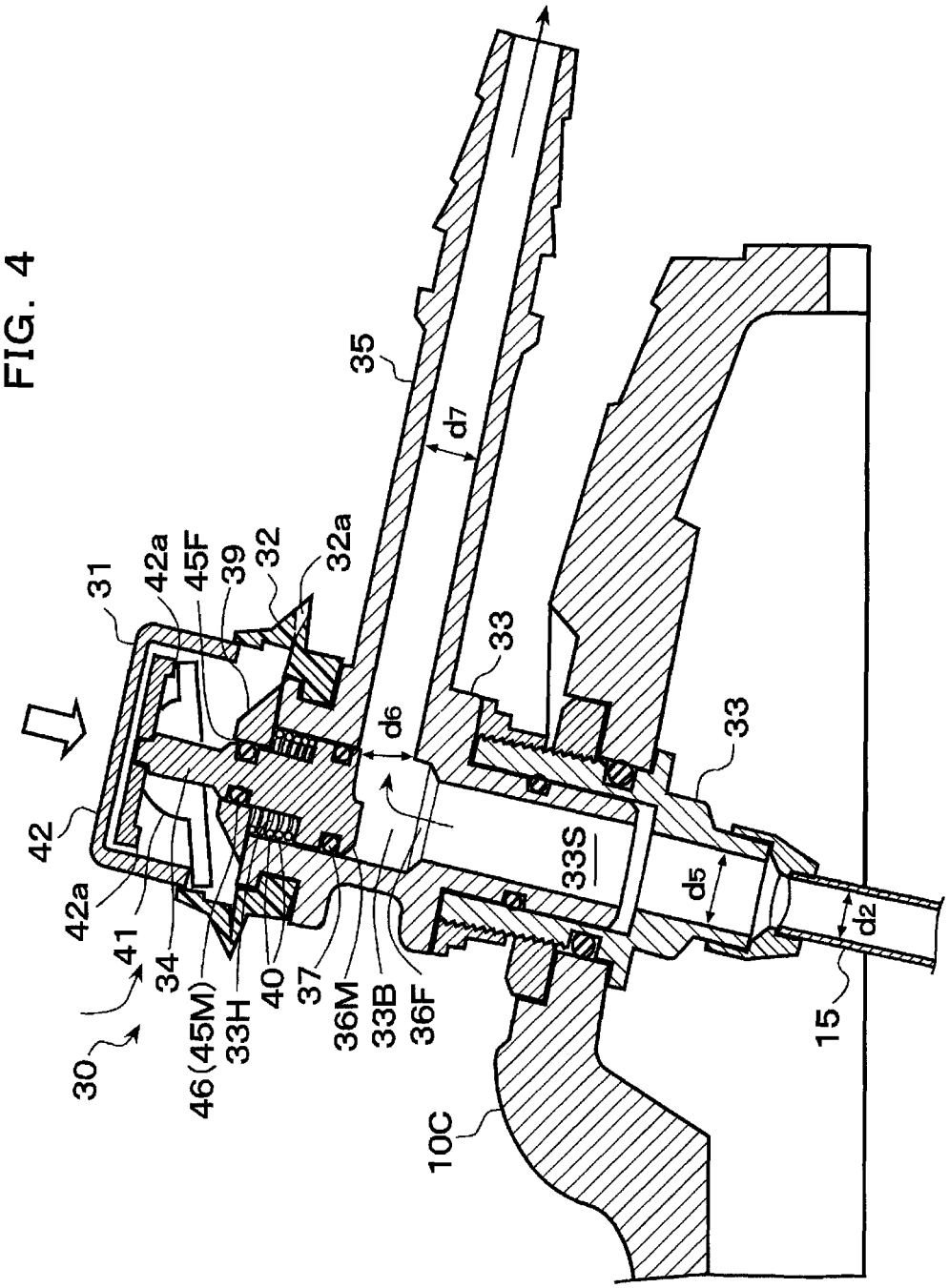
FIG. 4 is a sectional view illustrating a configuration of an open state of the suction valve of the second embodiment.

FIGS. 3 and 4 show a configuration of a suction valve portion according to a second embodiment, and this second embodiment is configured such that a reverse movement mechanism is disposed so that a piston shaft is moved to the side opposite to the pressing direction.

As shown in the figures, in a suction valve 30, a button holding portion 32 that holds a suction button 31 and is made of a telescopic and cylindrical elastic member and a main body 33 that supports this holding portion 32 are disposed, and in the holding portion 32, an opening 32a for inflow of the air is formed. Inside the main body 33, a reciprocally moving piston body 34 is arranged, an air passage 33H is formed on the outer peripheral side of this piston body 34, and a valve-portion passage (internal passage) 33S so as to communicate with this air passage 33H to become a suction tube is formed.

Also, on the upper part of this valve-portion passage 33S, a bending passage (which is a valve-portion passage) 33B for bending the passage toward the side face of the main body 33 is formed, and a connection tube 35 is arranged so as to communicate with this bending passage 33B. And a valve receiving portion 36F is disposed at a base end portion of the bending passage 33B, and a valve movable portion 36M is disposed having an O-ring 37 at the lower end of the piston shaft 34 so as to be in close contact with this valve receiving portion 36F and to close the valve-portion passage 33S.

On an upper face portion of the main body 33, a supporting fixed plate 39 having a disk shape and a center through hole is fixed and arranged, and between this supporting fixed plate 39 and the lower end portion of the piston shaft 34, a coil spring 40 is disposed that urges this piston shaft 34 to a pressing operation direction with respect to the supporting fixed plate 39. This supporting fixed plate 39 also functions as a supporting portion for two reversing levers 41 (only one of them is shown in the figure), and this reversing lever 41 has its rotation shaft pivotally supported by a pivotal support portion of the supporting fixed plate 39. That is, this reversing lever 41 has its rotation shaft arranged substantially coaxially with the shaft of the suction button 31 in the operation direction or the piston shaft 34 and has the lever shorter from the rotation shaft to one end and the lever longer to the other end in order to perform a reversing operation by the principle of leverage.

On the other hand, on the upper side of this supporting fixed plate 39, a connecting body 42 is mounted and fixed to the upper part of the piston shaft 34, and this connecting body 42 is arranged so that the shorter lever ends of the reversing levers 41 (two units) are engaged with/connected to two engagement claws 42a protruding in the horizontal direction at the both end portions thereof. With the longer lever ends of the reversing levers 41, a lower end portion of the suction button 31 is engaged, and the two reversing levers 41 move the piston shaft 34 to the side opposite to the pressing operation direction through the connecting body 42 by a pressing operation on the suction button 31.

Moreover, in the center opening portion of the supporting fixed plate 39, a valve receiving portion 45F of a valve portion for air passage is disposed, and a valve movable portion 45M is disposed having an O-ring 46 in an intermediate portion of the piston shaft 34 so as to be in close contact with the valve receiving portion 45F and to close the air passage 33H.

In this second embodiment, too, a diameter $d_5$ of the valve-portion passage 33S in the suction valve 30 is set at $\phi 3.5$, and the bottom face portion of the piston shaft 34 is cut away in the bending passage 33B, which is the valve-portion passage, whereby a diameter of the bending passage 33B (diameter of the minimum portion) $d_6$ is set at $\phi 3.4$, so that they are larger than the inner diameter $d_2$ ($=\phi 3.2$) of the suction tube 15 and an inner diameter $d_7$ ($=\phi 3.2$) of the connection tube 35. That is, the minimum diameter of the valve-portion passage 33S including the bending passage 33B is made larger than the diameter $d_2$ of the suction tube 15 and the forceps diameter $d_1$.

The second embodiment is configured as above, and when the suctioning is not operated in FIG. 3, since the valve movable portion 36M and the valve receiving portion 36F of the valve portion for the suction tube are closed, and the valve movable portion 45M in the valve portion for the air passage is separated from the valve receiving portion 45F and is open, the air having flown through the opening 32a of the holding portion 32 passes through the air passage 33H in the main body 33 and is led to the connection tube 35.

On the other hand, if the suction button 31 is pressed as shown in FIG. 4, the longer lever end of the reversing lever 41 is pressed down, and by means of a see-saw operation and the principle of leverage, the shorter lever end of this reversing lever 41 is raised, whereby the piston shaft 34 connected through the connecting body 42 is moved (reverse movement) in a direction opposite to the pressing operation direction against the urging force of the spring 40. At this time, the valve movable portion 36M for the suction tube is separated from the valve receiving portion 36F, the valve portion for the suction tube is opened so that suctioning is performed, and the suctioned substances are discharged from the suction tube 15 through the valve-portion passage 33S, the bending passage 33B, the connection tube 35, and the external suction tube 18 into the preserving tank 19. After that, by releasing the suction button 31, the piston shaft 34 is pressed down by the spring 40, and the suction button 31 is automatically returned to the original position.

With the configuration of this second embodiment, too, by setting such that the forceps diameter $d_1$<diameter $d_2$ of the suction tube 15<diameter $d_5$ of the valve-portion passage 33S and the diameter $d_6$ of the bending passage 33B, solid substances and substances with high viscosity can be smoothly suctioned, and clogging in the suction tube 15 and the suction valve 30 can be prevented.

By taking a sufficient pressing-down distance for the suction button 31, the reverse movement distance of the piston shaft 34 can be sufficiently ensured, and the diameter $d_6$ of the bending passage 33B can be taken wider than the forceps diameter $d_1$. On the other hand, in the second embodiment, a portion below the O-ring 37 of the piston shaft 34 and on the side of the connection tube 35 is notched in the configuration. As a result, the pressing-down distance of the suction button 31 required for the suctioning operation is reduced so as to alleviate the burden of the operator, while the diameter $d_6$ of the bending passage 33B can be taken wider than the forceps diameter $d_1$. Since the portion to be cut away is a portion below the O-ring 37, it does not affect air tightness during the suctioning operation.

Figure 5:
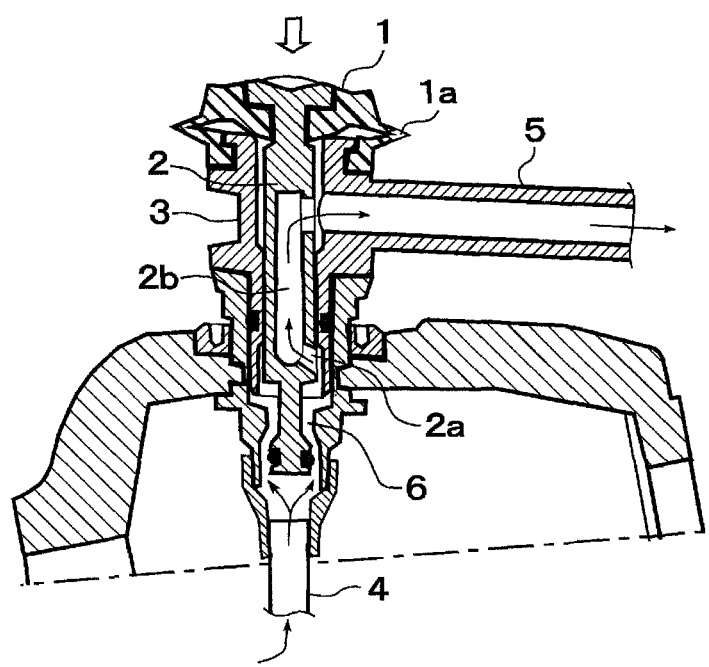
FIG. 5 is a sectional view illustrating a configuration (open state) of a prior-art suction valve.

In the suction valves 16 and 30 in the above embodiment, there is no passage between the side faces of the piston shafts 24 and 34 and the valve-portion passages 25a and 33S, but as described in FIG. 5, there is a suction valve having a passage between the side face of the piston shaft and the valve-portion passage. In this case, it can be so configured that the passage between the side face of the piston shaft and the valve-portion passage is made wider than before, while the diameter $d_2$ of the suction tube can be made larger than the forceps diameter $d_1$. That is, by making the diameters of the tube and the passage from the suction tube 15 to the preserving tank 19 larger than the forceps diameter $d_1$, the suction load is made smaller than before, and such an advantage can be obtained that clogging by the suctioned substances can be prevented.

Description of Symbols 2, 24, 34 PISTON SHAFT, 3, 25, 33 MAIN BODY
4, 15 SUCTION TUBE, 5, 17, 35 CONNECTION TUBE
10C OPERATION PORTION,
13 TREATMENT INSTRAMENT INSERTION CHANNEL,
16, 30 SUCTION VALVE, 18 EXTERNAL SUCTION TUBE,
23, 31 SUCTION BUTTON, 24a INNER-SHAFT,
25a, 33S VALVE-PORTION PASSAGE, 41 REVERSING LEVER Citation List
Patent Document 1: JP-A-2007-185276
Patent Document 2: JP-A-2004-223121

The invention claimed is:
1. A suction conduit device of an endoscope, comprising:
a treatment instrument insertion channel arranged from a distal end portion to an operation portion of the endoscope;
a suction conduit disposed from the treatment instrument insertion channel in the operation portion through a branch portion for suctioning a target substance through the treatment instrument insertion channel; and
a suction valve that opens/closes the conduit by reciprocally moving a piston shaft through a valve-portion passage to which the suction conduit is connected and does not use a space between the valve-portion passage and a side face of the piston shaft and an inner-shaft passage formed in the piston as a passage but uses only the valve-portion passage as a passage, wherein a diameter of the valve-portion passage of the suction valve is made larger than a diameter of the suction conduit, and wherein the suction valve is configured such that a bending passage is disposed as the valve-portion passage, and the suction valve has a bottom of the piston shaft so that the bottom of the piston shaft closes/opens one passage side of the bending passage.

2. The suction conduit device of an endoscope according to claim 1, wherein the diameter of the suction conduit is made larger than a diameter of the treatment instrument insertion channel arranged on the distal end side from the branch portion.

3. The suction conduit device of an endoscope according to claim 1, wherein the suction valve is configured such that a reversal movement mechanism that moves the piston shaft to the side opposite to the pressing direction of the suction button is disposed, and a bending passage is also disposed as a valve-portion passage of the suction valve so that the piston shaft is reciprocally moved with respect to this bending passage so as to open/close the valve; and the diameter of the valve-portion passage is ensured by cutting away a bottom face portion of the piston shaft.

4. The suction conduit device of an endoscope according to claim 1, wherein the suction valve is configured such that a reversal movement mechanism that moves the piston shaft to the side opposite to the pressing direction of the suction button is disposed, so that, when the suction button is pressed, the suction valve is opened by moving the piston shaft to the side opposite to the pressing direction.

* * * * *